(12) United States Patent
Pa et al.

(10) Patent No.: US 10,119,638 B2
(45) Date of Patent: Nov. 6, 2018

(54) FLUIDIC COUPLING DEVICES, ASSEMBLIES, AND RELATED METHODS

(71) Applicant: Agilent Technologies, Inc., Santa Clara, CA (US)

(72) Inventors: Ponna Peter Pa, Bear, DE (US); Lindy T. Miller, West Chester, PA (US); Tirzah Vogels, Phoenixville, PA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 453 days.

(21) Appl. No.: 14/766,106

(22) PCT Filed: Dec. 6, 2013

(86) PCT No.: PCT/US2013/073545
§ 371 (c)(1),
(2) Date: Aug. 5, 2015

(87) PCT Pub. No.: WO2014/123618
PCT Pub. Date: Aug. 14, 2014

(65) Prior Publication Data
US 2015/0369402 A1    Dec. 24, 2015

Related U.S. Application Data

(60) Provisional application No. 61/761,410, filed on Feb. 6, 2013.

(51) Int. Cl.
*G01N 1/00* (2006.01)
*F16L 15/08* (2006.01)
(Continued)

(52) U.S. Cl.
CPC .............. *F16L 15/08* (2013.01); *F16L 49/06* (2013.01); *G01N 30/6026* (2013.01); *G01N 30/6039* (2013.01)

(58) Field of Classification Search
CPC ...................................................... G01N 1/00
See application file for complete search history.

(56) References Cited

U.S. PATENT DOCUMENTS

| 5,163,722 A | 11/1992 | Worden |
|---|---|---|
| 5,234,235 A | 8/1993 | Worden |

(Continued)

FOREIGN PATENT DOCUMENTS

| CN | 101313164 A | 11/2008 |
|---|---|---|
| CN | 101617162 A | 12/2009 |

(Continued)

OTHER PUBLICATIONS

Chinese Office action dated Jul. 11, 2016 from related Chinese Application No. 201380072324.X.

(Continued)

*Primary Examiner* — Jyoti Nagpaul

(57) ABSTRACT

A fluidic coupling device includes a housing, and a piston, spring, and cap insertable in the housing. The spring includes a stack of spring washers and is compressible between the cap and the the piston. The cap is threadedly engageable with the housing and movable into contact with the spring. The device may be coupled to a component in a sealed manner by inserting a ferrule between the piston and the component, inserting a conduit through the housing and into the component, and threadedly engaging the housing with the component, thereby compressing the spring and translating the piston against the ferrule. The device may enable coupling to be done manually, with minimal variation in compressive loading. The piston and spring may desensitize the device to thermal cycling effects, reducing the need for retightening.

20 Claims, 14 Drawing Sheets

(51) Int. Cl.
*F16L 49/06* (2006.01)
*G01N 30/60* (2006.01)

(56) References Cited

U.S. PATENT DOCUMENTS

| | | |
|---|---|---|
| 5,595,406 A | 1/1997 | Warchol |
| 2007/0001451 A1 | 1/2007 | Struven |
| 2010/0171309 A1 | 7/2010 | Kainec |
| 2012/0223520 A1 | 9/2012 | Graham |

FOREIGN PATENT DOCUMENTS

| | | | |
|---|---|---|---|
| GB | 2 379 487 A | | 3/2003 |
| GB | 2379487 | * | 3/2003 |
| GB | 2379487 A | | 3/2003 |

OTHER PUBLICATIONS

The International Search Report for PCT/US2013/073545 dated Mar. 25, 2014.
Chinese Office action dated Apr. 1, 2017 from related Chinese Application No. 201380072324.X.

* cited by examiner

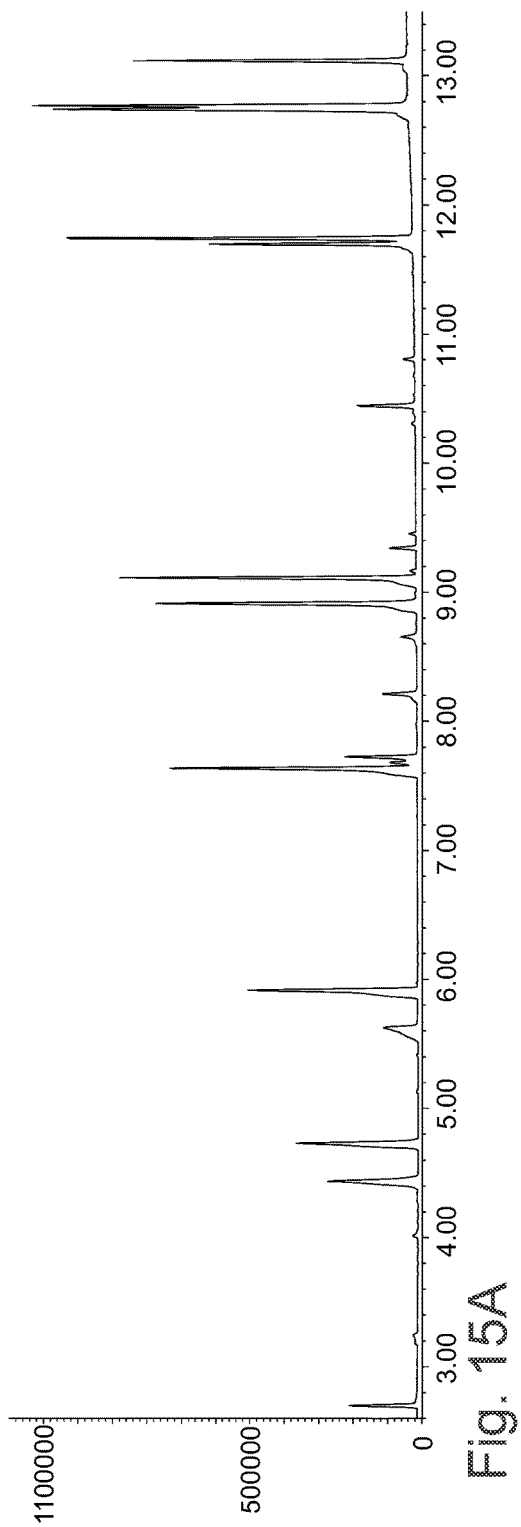
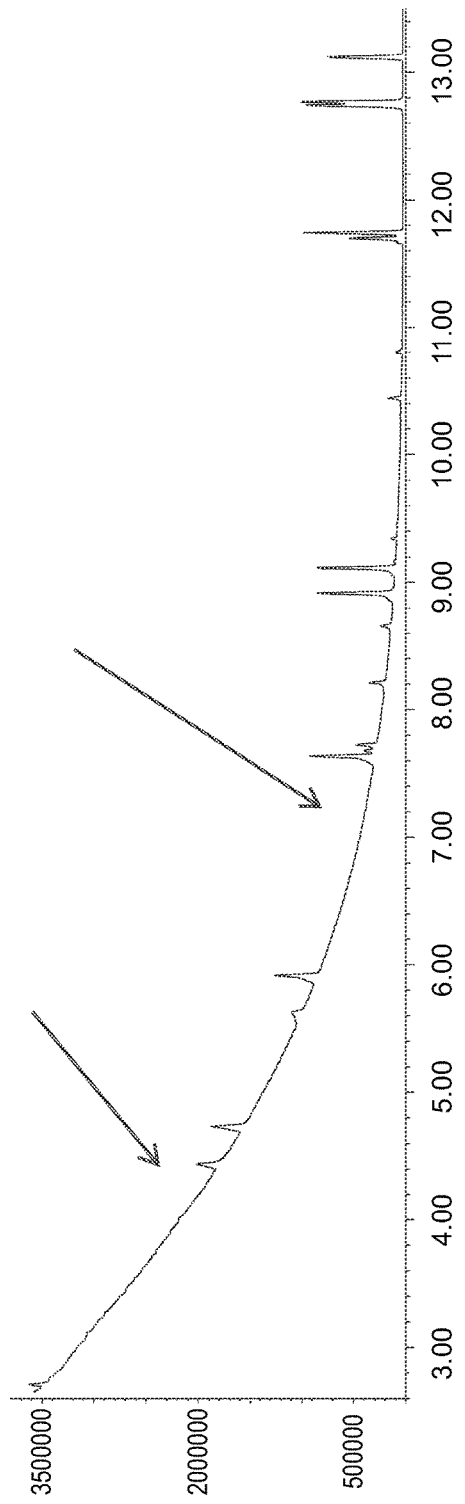
Fig. 15A
Fig. 15B

FLUIDIC COUPLING DEVICES, ASSEMBLIES, AND RELATED METHODS

RELATED APPLICATIONS

This application is the national stage of International Application No. PCT/US2013/073545, filed Dec. 6, 2013, titled "FLUIDIC COUPLING DEVICES, ASSEMBLIES, AND RELATED METHODS," which claims the benefit of U.S. Provisional Patent Application Ser. No. 61/761,410, filed Feb. 6, 2013, titled "FLUIDIC COUPLING DEVICES, ASSEMBLIES, AND RELATED METHODS," the contents of both of which are is incorporated by reference herein in their entireties.

TECHNICAL FIELD

The present invention relates generally to fluidic couplings, particularly fluidic couplings entailing the use of ferrules.

BACKGROUND

Ferrules may be utilized to form leak-free fluidic couplings between two components. Ferrules may be employed in applications entailing small-scale fluid flows, such as analytical instruments and microfluidic devices, and thus may be sized to join a small-bore conduit such as a capillary tube or fitting with another component, or to create a sealed connection between two conduits with the use of a union or tee connection. The coupling may be established by a solid-to-solid seal that is secured by mating two surfaces together, one of which is an outer surface of the ferrule. The coupling may be formed under mechanical compression achieved by applying torque to a compression nut or equivalent component such that the nut bears against the ferrule. Depending on design, torque may be applied manually (i.e., hand-tightening or finger-tightening) or with the aid of a wrench or other tool.

In a typical example of a conventional fluidic coupling utilizing a ferrule, a conduit is inserted through the bore of the ferrule and the conduit and ferrule are inserted into the interior of a union or other structure with which the ferrule is to form a sealed interface. The conduit also passes through a compression nut. The nut is threaded onto the union and rotated (screwed). Rotation axially translates the nut directly into the contact with the ferrule. Consequently, the ferrule is axially translated into contact with an inside surface of the union under a compressive force imparted by rotation of the nut, thereby creating a sealed interface between the ferrule and the inside surface against which the ferrule bears. The ferrule may also be shaped so that the compressive load also causes the ferrule to bear against the portion of the conduit residing in the ferrule's bore.

This type and other types of conventional fluidic couplings have disadvantages. A conventional fluidic coupling provides no mechanism for a user to feel and limit the torque or force developed during rotation of the nut, which may result in a wide variation of compressive loads applied by users from one coupling site to another. Moreover, depending on the system or environment in which the fluidic coupling operates, the fluidic coupling may be subjected to thermal cycling. The thermal cycling may be significant, ranging for example from −80° C. (cryogenic liquid $N_2$) to 400° C. Thermal cycling may cause thermal expansion and contraction of the solid components, and material relaxation due to annealing. Hence, thermal cycling may adversely affect the reliability of sealing interfaces. In particular, thermal cycling may reduce the sealing pressure at the solid-to-solid interfaces and thus cause undesirable fluid leakage, requiring the nut to be retightened to reestablish the sealing pressure or in some cases requiring one or more components of the coupling assembly to be replaced. The sealing pressure is proportional to the compressive load maintained on the solid-to-solid interface. Such an interface is very sensitive to the level of contact pressure being applied because there is very little elasticity in the system. Thus, a slight reduction in pressure due to thermal cycling or other causes may result in fluid leakage.

In general, there is an ongoing need for improving fluidic couplings. There is also a need for providing a fluidic coupling that enables compression to be applied consistently, without needing to measure torque or compressive load. There is also a need for providing a fluidic coupling that maintains reliable sealing interfaces over many cycles of operation before requiring maintenance. There is also a need for providing a fluidic coupling that minimizes sensitivity to thermal cycling.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a fluidic coupling device, includes: a housing including a first housing end, a second housing end, and a housing bore extending along an axis from the first housing end to the second housing end; a ferrule including a tapered outer surface and insertable into the housing bore; a piston insertable into the housing bore such that the piston contacts the ferrule; a spring including an axial series of spring washers and insertable into the housing bore such that the piston is between the spring and the ferrule; and a cap insertable into the housing bore and into contact with the spring, the cap being threadedly engageable with the first housing end, wherein rotation of the cap or the housing compresses the spring and translates the piston against the ferrule such that the tapered outer surface and a tapered inner surface are compressed together, and wherein the tapered inner surface is selected from the group consisting of: a tapered inner surface of the piston; and a tapered inner surface of a body attachable to the second housing end.

According to another embodiment, the fluidic coupling device includes a gripping component extending outward from the housing and configured for gripping by a user to facilitate manual rotation of the housing.

According to another embodiment, the piston includes the tapered inner surface, and rotation of the cap or the housing translates the tapered inner surface into contact with the tapered outer surface.

According to another embodiment, the body includes the tapered inner surface, and rotation of the cap or the housing translates the tapered outer surface into contact with the tapered inner surface.

According to another embodiment, the fluidic coupling device includes a first conduit extending through respective bores of the first cap, the first spring, the first piston and the first ferrule, wherein compression of the first tapered outer surface and the first tapered inner surface together compresses the first ferrule against the first conduit; and a second conduit extending through respective bores of the second cap, the second spring, the second piston and the second ferrule, wherein compression of the second tapered outer surface and the second tapered inner surface together compresses the second ferrule against the second conduit, and the first conduit and the second conduit are in fluid communication along the axis.

According to another embodiment, a fluidic coupling kit includes a fluidic coupling device. The components of the fluidic coupling device may include a housing, a piston, a spring and a cap. The components may all be disassembled, one or more components may be assembled together, or all components may be assembled together. In some embodiments, the fluidic coupling kit may include one or more ferrules. In some embodiments, the fluidic coupling kit may include one or more conduits.

According to another embodiment, a fluidic assembly includes: a fluidic coupling device; a body including a body bore and threadedly engageable with the second housing end; and a conduit extending through respective bores of the cap, the spring, the piston, and the ferrule such that the conduit communicates with or extends into the body bore, wherein rotation of the housing relative to the body compresses the tapered outer surface and the tapered inner surface together to form a fluidic seal therebetween, and compresses the ferrule against the conduit.

According to another embodiment, the body is part of an analytical instrument.

According to another embodiment, the conduit and/or the body bore communicates with an ionization chamber.

According to another embodiment, a fluidic coupling device includes: a housing including a first housing end, a second housing end, a housing bore extending along an axis from the first housing end to the second housing end, and a first passage oriented at an angle to the axis; a piston disposed in the housing bore; a spring including an axial series of spring washers disposed in the housing bore; a cap disposed in the housing bore wherein the spring is between the cap and the piston, the cap including a second passage and threadedly engaged with the first housing end to a locked position at which the first passage is aligned with the second passage; and a pin extending through the first passage and the second passage, wherein the pin retains the cap in the locked position.

According to another embodiment, a fluidic coupling kit includes: one or more fluidic coupling devices; and a body including a first body end, a second body end, and a body bore extending along the axis from the first body end to the second body end, wherein the second housing end of each fluidic coupling device is threadedly engageable with a selected one of the first body end and the second body end.

According to another embodiment, a method for making a fluidic coupling includes: inserting a ferrule into a fluidic coupling device, the fluidic coupling device including a housing, a piston, a spring including an axial series of spring washers, and a cap, wherein the piston is disposed in the housing between the spring and the ferrule, and the cap is threadedly engaged with a first housing end of the housing; inserting a conduit through respective bores of the cap, the spring, the piston and the ferrule; threadedly engaging a second housing end of the housing with a body such that the conduit extends into an interior of the body; and forming a fluidic seal between the ferrule and the piston and between the ferrule and the body by rotating the housing relative to the body, wherein rotating the housing compresses the spring between the cap and the piston, compresses the ferrule against the conduit, and compresses a tapered outer surface of the ferrule against a tapered inner surface, and wherein the tapered inner surface is selected from the group consisting of: a tapered inner surface of the piston; and a tapered inner surface of a body attachable to the second housing end.

According to another embodiment, a method for assembling a fluidic coupling device includes: inserting a piston into a housing bore of a housing, wherein the housing bore extends along an axis; inserting a spring including an axial series of spring washers into the housing bore; threadedly engaging a cap with the housing such that the spring is between the cap and the piston; and rotating the cap relative to the housing to translate the cap axially toward the spring.

According to another embodiment, the housing includes a first passage oriented at an angle to the axis, and the cap is rotated until a second passage of the cap is aligned with the first passage. The cap is retained in a locked position by inserting a pin through the first passage and the second passage.

According to another embodiment, rotating the cap to the locked position compresses the spring between the cap and the piston.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 15A is a chromatogram acquired from initial testing of a fluidic coupling device having a known configuration that was newly installed in a GC-MS system.

FIG. 15B is a chromatogram acquired during the same testing referred to above in conjunction with FIG. 15A, after subjecting the fluidic coupling device of known configuration to 25 thermal cycles.

DETAILED DESCRIPTION

In the present context, the term "conduit" may encompass any type of tube through which a fluid may flow. In some embodiments, the conduit may have an inside or outside diameter on the millimeter- or micrometer-scale (e.g., capillary tubes, small-bore chromatographic columns, etc.).

In the present context, the term "ferrule" may encompass any type of fluidic connector, i.e., a component designed to form a fluidic connection between two conduits. The resulting fluidic connection is typically fluid-tight within a specified range of intended operating pressures. The ferrule may be sized to form a joint with a conduit, or between two conduits, having diameters on the millimeter- or micrometer-scale, in which case the ferrule may be considered as being a microfluidic connector. In some small-scale examples, the ferrule has a length ranging from 1 to 10 mm, a maximum outer diameter ranging from 1 to 10 mm, and a bore size (inside diameter) ranging from 0.1 to 2 mm. As a further example, the ferrule may be sized to receive a gas chromatograph (GC) column. In typical applications, GC columns have internal diameters ranging from 50-530 μm. In some examples, the ferrule may have two bores running through its length. The ferrule may be configured for joining conduits, or joining a conduit with another hollow component, composed of dissimilar materials (e.g., fused silica glass and metal) and/or different diameters. As one non-limiting example, the ferrule may be utilized in conjunction with analytical instrumentation such as chromatography- or spectrometry-based systems. The ferrule may be designed to operate as a compression fitting. In this case, a conduit may be inserted into the ferrule's inner bore, or two conduits may be inserted into the opposite ends of the ferrule's inner bore, and an appropriate technique is then implemented to compress or clamp the ferrule onto the conduit(s) to form a fluidic seal, such as by employing a compression nut or a tool. The ferrule may also be configured as a three-way connector.

Figure 1:
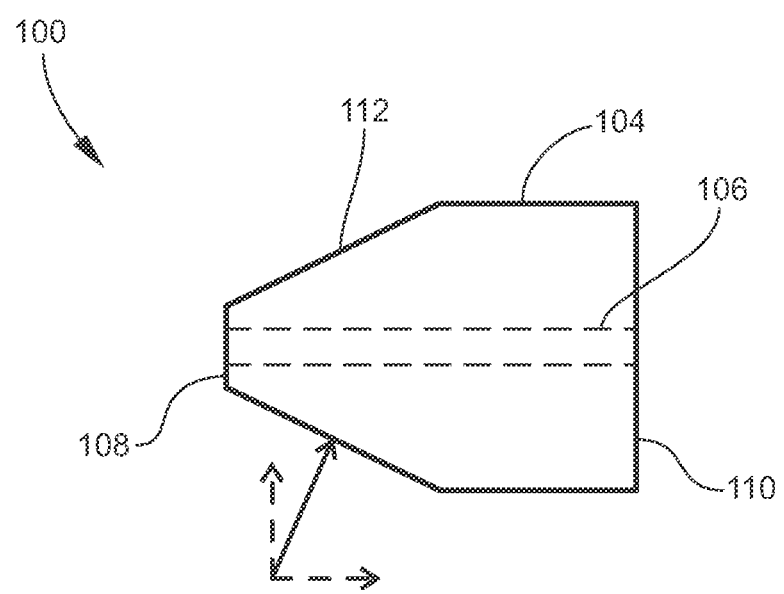
FIG. 1 is a side view of an example of a ferrule.

FIG. 1 is a side view of an example of a ferrule 100. The ferrule 100 typically includes a body of circular cross-section. The body includes an outer surface 104 and an axial ferrule bore 106 extending between two axially opposing ferrule end surfaces 108 and 110. The outer surface 104 typically includes a tapered (e.g., conical) outer surface 112. The tapered outer surface 112 enables the ferrule 100 to be compressed against the surface of another structure (not shown) with a force that has both axial and radial components relative to the axis, as shown by arrows. The surface against which the tapered outer surface 112 is compressed may or may not also be tapered. If the surface against which the tapered outer surface 112 is compressed is tapered, it may be tapered at a different angle than the tapered outer surface 112. The ferrule 100 may be composed of a polymer or soft metal having a degree of deformability suitable for making a fluidic coupling by manual force (e.g., by hand-tightening a compression nut). Alternatively, the ferrule 100 may be composed of a hard metal in which case a tool such as a wrench may be employed in making a fluidic coupling (e.g., by swaging).

Figure 2:
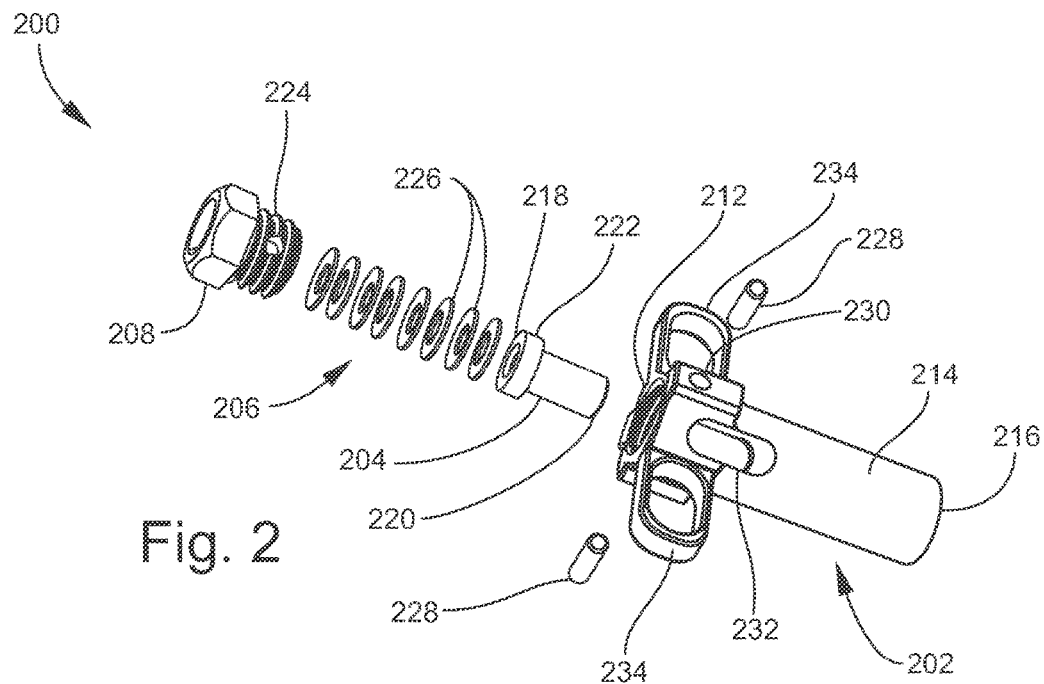
FIG. 2 is an exploded perspective view of an example of a fluidic coupling device according to one embodiment.
Figure 3:
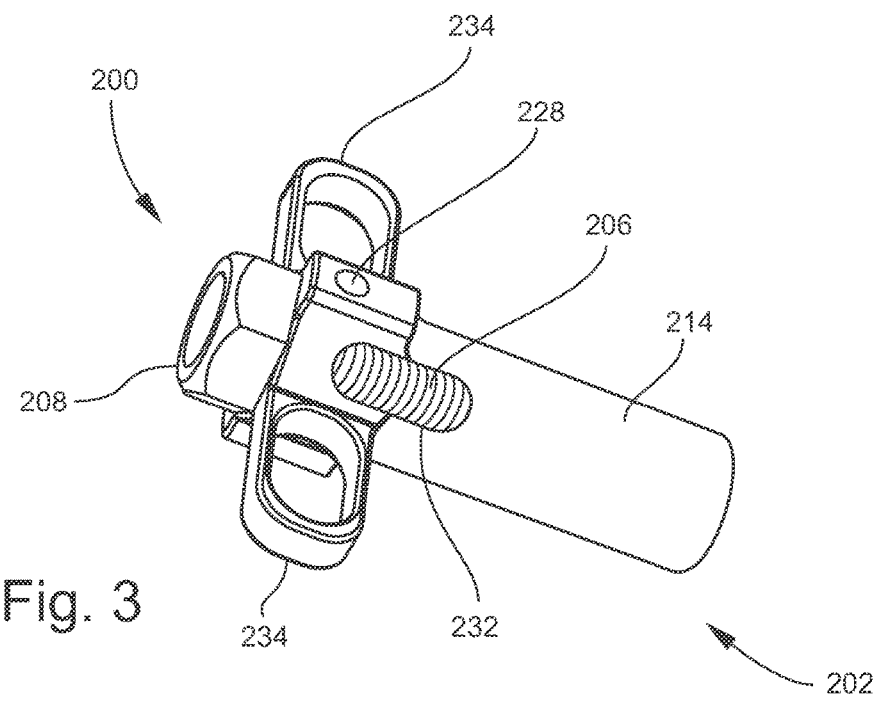
FIG. 3 is an assembled perspective view of the fluidic coupling device illustrated in FIG. 2.

FIG. 2 is an exploded perspective view of an example of a fluidic coupling device 200 according to one embodiment. FIG. 3 is an assembled perspective view of the fluidic coupling device 200. The fluidic coupling device 200 may include a housing 202, a piston 204, a spring 206, and a cap 208. The housing 202 may include a first housing end 212, a second housing end 214, and a housing bore 216 extending along a longitudinal axis of the fluidic coupling device 200 between the first housing end 212 and the second housing end 214. The piston 204 may include a first piston end 218 and a second piston end 220. The piston 204 may include a piston head 222 of larger outer diameter than the rest of the piston 204. The cap 208 may include a threaded section 224 configured for engaging a threaded section (not shown) of the housing 202 at the first housing end 212. In the illustrated example, the cap's threaded section 224 is an outer section configured for mating with internal threads of the housing bore 216. Alternatively, the cap 208 may include internal threads configured for mating with external threads located at the outer surface of the first housing end 212. The housing 202 may also include a threaded section (internal or external threads, not shown) at the second housing end 214, which may be configured for engaging an external body (not shown) with which the fluid coupling device 200 is to interface.

The spring 206 may include a plurality of spring washers 226 arranged (stacked) in an axial series along the longitudinal axis. The spring washers 226 may be configured as Belleville washers, which may also be known as Belleville springs, cupped spring washers, conical spring washers, disc springs, or coned-disc springs. As appreciated by persons skilled in the art, a spring washer 226 of this type, or a portion of this spring washer 226, has a conical shape such that the spring washer 226 imparts an axial force when deformed. Any number of individual spring washers 226 may be provided as needed for attaining a desired overall spring constant or amount of deflection of the resulting spring 206. Moreover, the respective orientations of the individual spring washers 226 may be varied as needed for modifying the spring constant or deflection. That is, all of the spring washers 226 may be oriented in the same way, or the orientations of one or more of the spring washers 226 may alternate (i.e., the conical portions of two adjacent spring washers 226 may face each other).

To assemble the fluidic coupling device 200, the piston 204 is inserted into the housing bore 216, such as through the first housing end 212. In some embodiments, the travel of the piston 204 is limited by a protrusion or stop member (not shown) in the housing bore 216 against which the piston head 222 comes into contact. The protrusion may be, for example, an annular shoulder or one or more tabs. The spring 206 is then inserted into the housing bore 216 and into contact with the first piston end 218, i.e., the first spring washer in the series contacts the first piston end 218. The cap 208 is then inserted into the housing bore 216 by threadedly engaging the cap 208 with the housing 202. That is, rotation of the cap 208 axially translates the cap 208 in the housing bore 216 in the direction of the spring 206 and piston 204. With the cap 208 installed, the spring 206 is disposed between the cap 208 and the piston 204. The cap 208 may be rotated until coming into contact with the spring 206, i.e., the last spring washer in the series. In some embodiments, during assembly the cap 208 is rotated enough to compress (pre-compress) the spring 206 to some degree, which may be facilitated in embodiments in which the piston head 222 abuts a protrusion in the housing bore 216. After assembly, the fluidic coupling device 200 is ready for use in making a fluidic coupling with another component, examples of which are described below.

The piston 204, spring 206, and cap 208 may have respective bores aligned with each other in the housing 202 along the axis. These bores may be sized to receive a conduit, as described below.

In some embodiments, the fluidic coupling device 200 includes one or more pins 228, the housing 202 includes a like number of first pin passages 230, and the cap 208 includes one or more corresponding second pin passages (not shown). The first pin passages 230 and second pin passages may extend through the respective structures of the housing 202 and cap 208 at an angle (e.g., ninety degrees) to the longitudinal axis. In this embodiment, the cap 208 is rotatable (axially translatable) to a locked position. At the locked position, the first pin passage(s) 230 are aligned with the second pin passage(s), enabling the pin(s) 228 to be inserted into the first pin passage(s) 230 and second pin passage(s). The pin(s) 228 may be secured in any manner, such as by press-fitting, threading, etc. The locked position with the pin(s) 228 inserted fixes the axial position of the cap 208, preventing any further rotation thereof. The fluidic coupling device 200 may, for example, be configured such that the spring 206 is compressed (pre-compressed) to a desired degree at the locked position. Alternatively or additionally, the locked position may be utilized to fix the components of the fluidic coupling device 200 in an assembled state to facilitate shipping the fluidic coupling device 200 to user or initial handling of the fluidic coupling device 200 by the user in preparation for use.

In some embodiments, the housing 202 includes one or more lateral apertures 232 extending through the housing structure from the outside to the housing bore 216. The lateral aperture(s) 232 may be located adjacent to the installed spring 206. During use of the fluidic coupling device 200, the lateral aperture(s) 232 may facilitate convective heat transfer from the spring 206 and nearby structures to reduce the adverse effect of thermal cycling on the integrity of the fluidic seal(s) provided by the fluidic coupling device 200. The configuration of the spring 206 may also enhance heat removal from the fluidic coupling device 200, in that the multiple spring washers 226 may provide a large surface area for heat removal in a manner analogous to cooling fins.

In some embodiments, the housing 202 includes one or more gripping components 234 extending outwardly from the main structure of the housing 202. The gripping components 234 are configured to be manipulated by a user to facilitate rotation of the housing 202 relative to a component with which the housing 202 is threadedly engaged, during the process of making a fluidic coupling as described by example below. In the illustrated embodiment, the gripping components 234 are handles or wings. In another embodiment, the gripping component 234 may be an annular component (e.g., a knob, wheel, collar, etc.) affixed to the housing 202. The outer surface of the annular component may be configured to facilitate gripping by the user; for example, the outer surface may be knurled.

Figure 4:
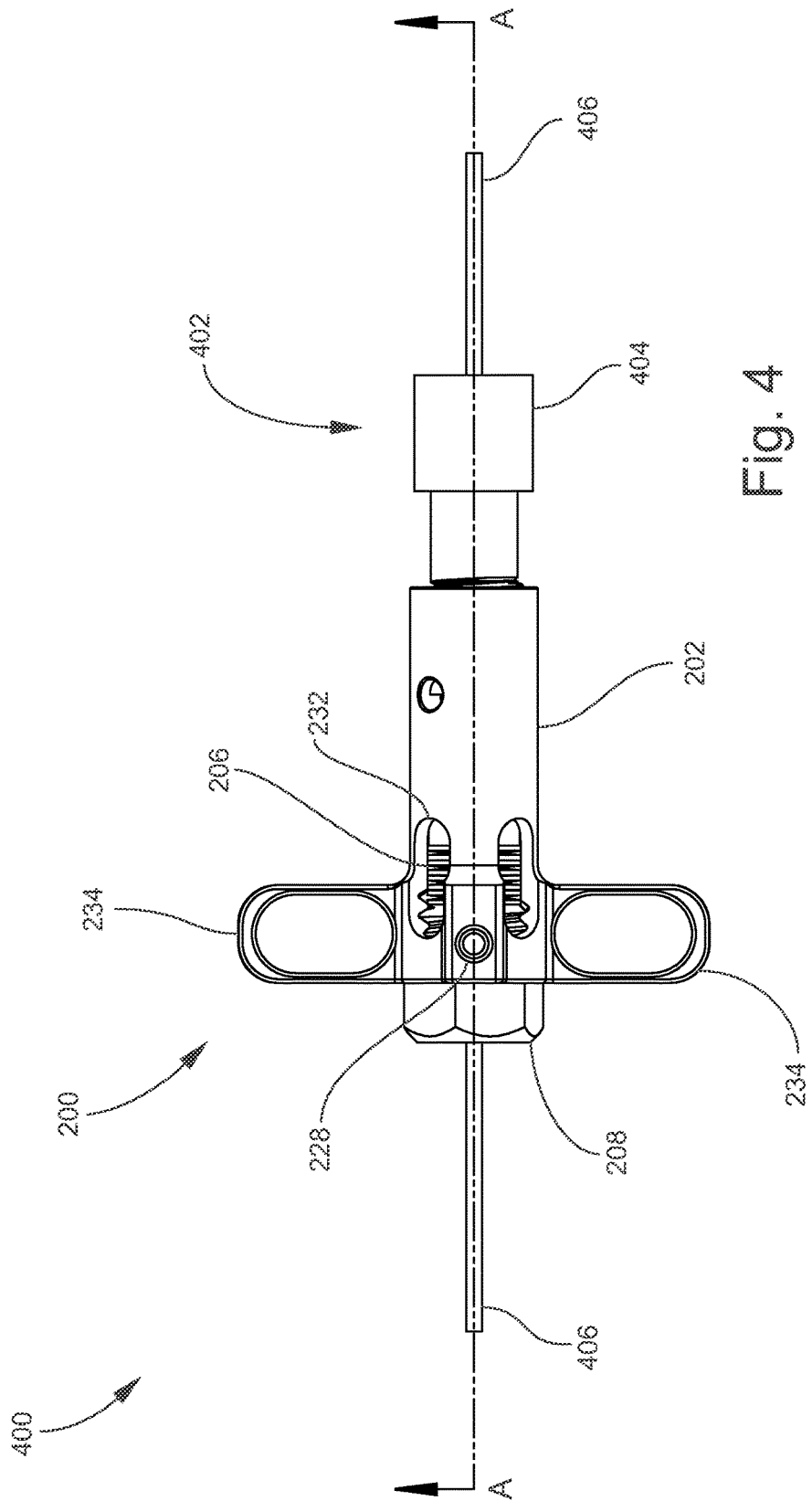
FIG. 4 is a side view of an example of a fluidic assembly formed by fluidly coupling the fluidic coupling device illustrated in FIGS. 2 and 3 to another component.

FIG. 4 is a side view of an example of a fluidic assembly or system 400 formed by fluidly coupling the fluidic coupling device 200 to another component 402. The component 402 may be or include a hollow body 404. A conduit 406 passes through the fluidic coupling device 200. Depending on the type of component 402 or fluid handling application being implemented, the conduit 406 may extend completely through the body 404 as illustrated, or may instead extend through a portion of the body 404 in open communication with the body's interior. As described by example below, a fluidic coupling or joint is made by creating sealed interfaces among the fluidic coupling device 200, the body 404, the conduit 406, and a ferrule 100 (e.g., FIG. 1).

In some embodiments, the body 404 is, is part of, or communicates with a chamber that is sealable in a fluid-tight manner. The chamber may require operation at a controlled pressure, which may be atmospheric pressure, above atmospheric pressure, or sub-atmospheric pressure (including, for example, very low pressure or vacuum). In such cases, the pressure in the chamber may be significantly different from the ambient pressure outside the chamber and/or the pressure inside the fluidic coupling device 200. As described below, the fluidic coupling device 200 is interfaced with the body 404 in a manner that provides one or more fluid-tight seals. The resulting sealing interface prevents fluid leakage (or pressure leakage) between the interiors of the fluidic coupling device 200 and the body 404, and leakage out from or into the fluidic coupling device 200 and the body 404. In some embodiments, the body 404 is part of an analytical instrument. As one non-limiting example, the body 404 may be associated with the inlet section of a mass spectrometer (MS). Continuing with this example, the body 404 may be part of or communicate with the ionization chamber (or "ion source") of an MS, and the conduit 406 may be the column of a gas chromatograph (GC) or may be a separate conduit that receives the output flow from an upstream GC column. The GC and its column may operate at around atmospheric pressure and, depending on type, the ionization chamber may operate at around atmospheric pressure or at a vacuum level. In either case, fluid leakage out from the ionization chamber or between the GC and the ionization chamber is undesirable.

Figure 5:
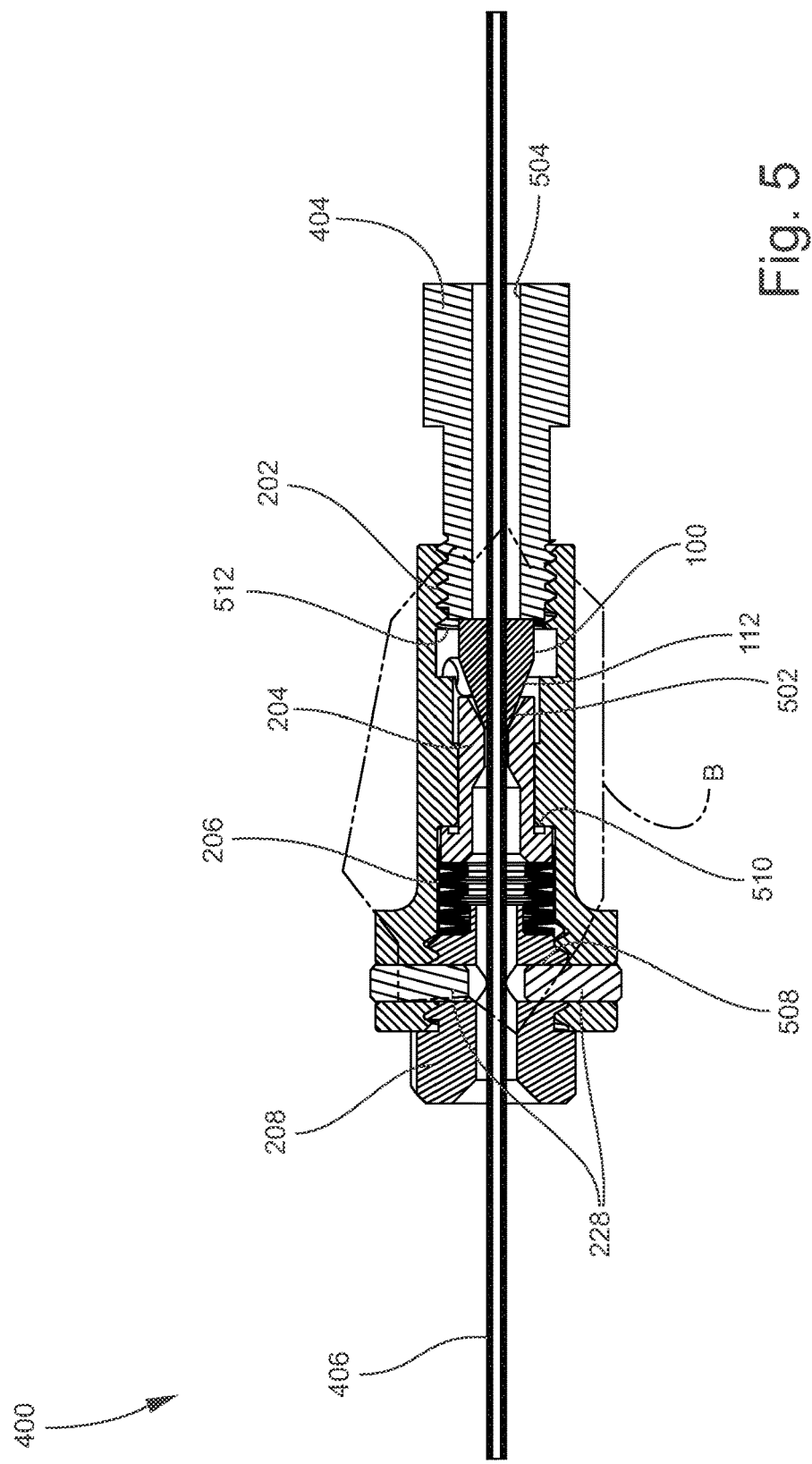
FIG. 5 is a cross-sectional view of the fluidic assembly taken along line A-A in FIG. 4.
Figure 6:
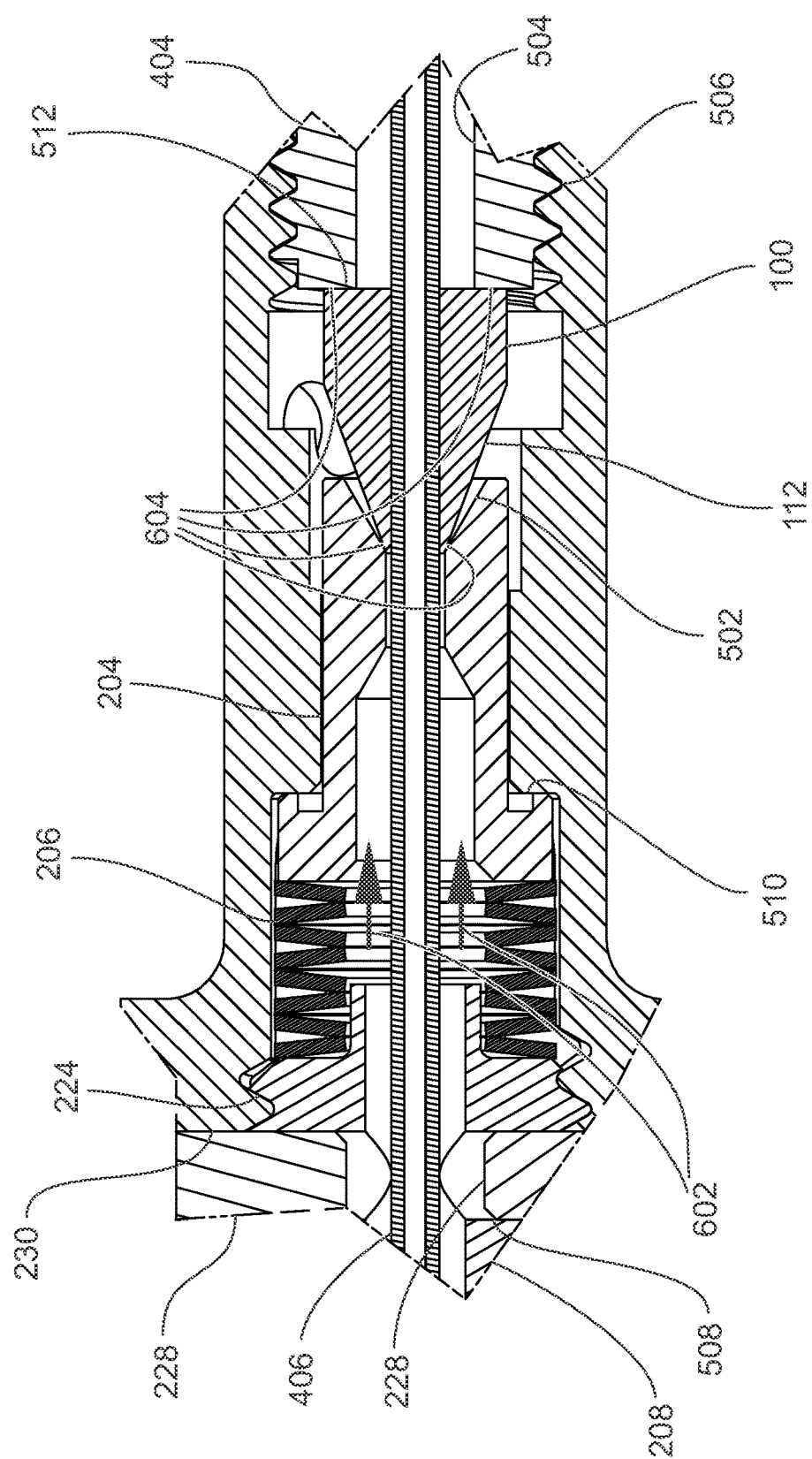
FIG. 6 is a detailed view of a region in FIG. 5 designated "B."

FIG. 5 is a cross-sectional view of the fluidic assembly 400 taken along line A-A in FIG. 4. FIG. 6 is a detailed view of a region in FIG. 5 designated "B." In this embodiment, the piston 204 includes a tapered (e.g., conical) inner surface 502 at the second piston end, which defines a portion of the piston bore. The tapered inner surface 502 is characterized by the diameter of the piston bore increasing in the direction toward the second piston end. The body 404 has a body bore 504 and a threaded section 506. In the illustrated embodiment, the threaded section 506 of the body 404 includes outer threads, and the second housing end includes inner threads configured to mate with the body's outer threads. Alternatively, the body 404 may include inner threads configured to mate with outer threads of the second housing end.

FIG. 5 also shows the cap 208 initially provided in the above-described locked position, at which the pin 228 is inserted through the first pin passage 230 of the housing 202 and a corresponding second pin passage 508 of the cap 208. FIG. 5 also shows a protrusion or stop member 510 in the housing bore. The head of the piston 204 may come into contact with the protrusion 510 to limit the extent of the piston's travel.

To make the fluidic coupling, a ferrule 100 is inserted into the housing bore from the second housing end, such that the ferrule's tapered outer surface 112 faces the piston's tapered inner surface 502. The conduit 406 is then inserted through the housing 202 from either the first housing end or second housing end. For example, the conduit 406 may be inserted through the cap bore, the spring bore (the successive bores of the spring washers), the piston bore, and the ferrule bore. The conduit 406 is then inserted into the body bore 504. The second housing end is then threadedly engaged with the body 404 and the housing 202 is rotated relative to the body 404, such as by manipulating one or more gripper elements 234 (FIG. 4) of the housing 202. Rotation of the housing 202 axially translates the piston 204 against the ferrule 100. In the illustrated embodiment, rotation of the housing 202 axially translates the tapered inner surface 502 against the tapered outer surface 112. In turn, rotation of the housing 202 axially translates the ferrule end surface opposite to the tapered outer surface 112 against a body surface 512 of the body 404, which for alignment purposes may be part of a seat sized to receive the ferrule 100. Rotation of the housing 202 compresses the spring 206, which imparts an axial compression force as depicted by arrows 602 in FIG. 6. Rotation of the housing 202 also causes the tapered inner surface 502 and the tapered outer surface 112 to be compressed together to form a fluidic seal therebetween, and the ferrule end surface and the body surface 512 to be compressed together to form a fluidic seal therebetween. The fluidic seals are depicted by regions or contact points 604 in FIG. 6. This compression in turn causes the ferrule 100 to bear down on the conduit 406.

The fluidic coupling device 200 (e.g., the piston 204 and spring 206) may be configured such that the maximum extent of rotation of the housing 202 required to form adequate fluidic seals may be determined by "feel." That is, rotation of the housing 202 causes deformation of the spring washers 226, and this deformation will eventually cease (e.g., all spring washers 226 will eventually flatten out to the same degree). The cessation in the deformation is tactile and discernible by the user, and thus may indicate to the user that adequate fluidic seals have been achieved such that further rotation is not needed. In this way, the fluidic coupling device 200 is configured to minimize variation in the compressive load applied when coupling the fluidic coupling device 200 to a component such as the body 404. That is, multiple fluidic coupling devices 200 may be utilized to make respective connections with different components, with the expectation that largely the same compressive load or torque will be applied by the user. Different users may learn or be instructed to use the same maximum feel to consistently apply the same load to a coupling site, without needing the aid of a torque measuring instrument or other instrument. The fluidic coupling device 200 may thus enable the fluidic sealing process to be less user dependent as compared to known devices.

An example of a fluidic coupling device consistent with the fluidic coupling device 200 described above and illustrated in FIGS. 2-6 has been subjected to thermal cycling tests using a plastic (graphite/Vespel® polymer) ferrule. The tests indicated that the fluidic coupling device 200 maintains a reliable fluidic seal over several cycles (e.g., thirty or more) before requiring retightening. It has been shown that the spring 206 continues to apply good and reliable sealing pressure to the ferrule regardless of thermal expansion or contraction or material relaxation. The floating piston 204 with the compact loaded spring system on one side reduces the sensitivity of the sealing pressures attained in the fluidic coupling device 200 to temperature changes and material changes caused by temperature changes.

The hand-tightening of the fluidic coupling device 200, i.e., manual rotation of the housing 202, which may be aided by using the optional gripping element 234, is generally a viable method when employing a ferrule composed of a polymer or a sufficiently deformable soft metal. In addition to rotating the housing 202, the cap 208 may be rotated relative to the housing 202 to apply compressive force. If the cap 208 is initially in a locked position as described above, the pin(s) 228 may need to be removed to enable further rotation of the cap 208. The fluidic coupling device 200 is also compatible for use with hard metal ferrules, in which case rotation of the cap 208 with the use of a tool may be required. The cap 208 may, for example, include flats (e.g., like a hex bolt) for gripping by a wrench.

Figure 7:
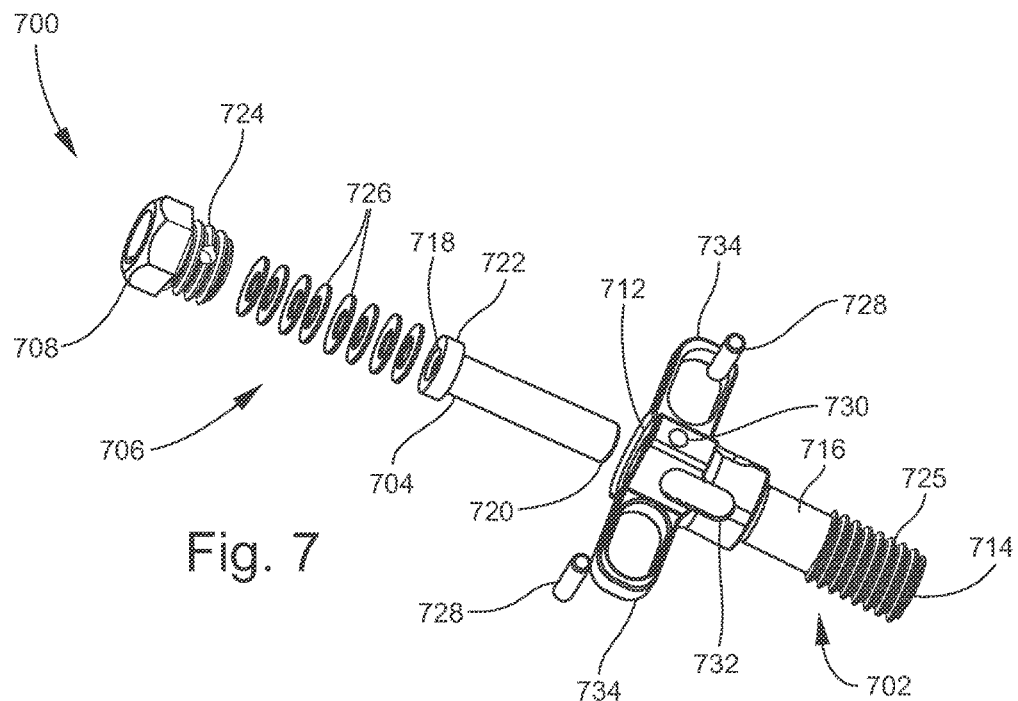
FIG. 7 is an exploded perspective view of an example of a fluidic coupling device according to another embodiment.
Figure 8:
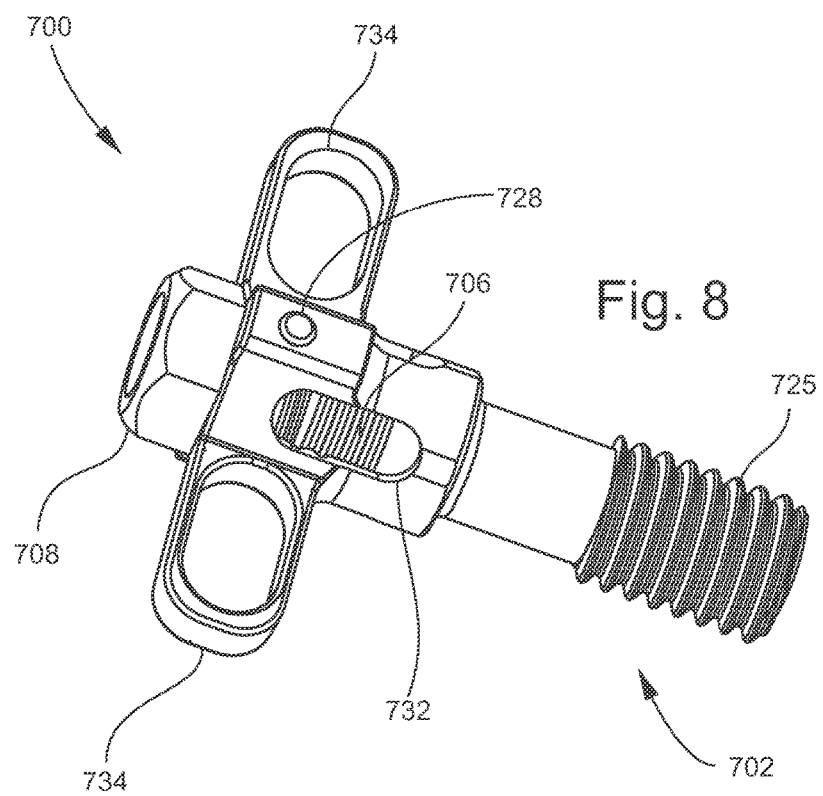
FIG. 8 is an assembled perspective view of the fluidic coupling device illustrated in FIG. 7.

FIG. 7 is an exploded perspective view of an example of a fluidic coupling device 700 according to another embodiment. FIG. 8 is an assembled perspective view of the fluidic coupling device 700. The fluidic coupling device 700 may include a housing 702, a piston 704, a spring 706, and a cap 708. The housing 702 may include a first housing end 712, a second housing end 714, and a housing bore 716 extending along a longitudinal axis of the fluidic coupling device 700 between the first housing end 712 and the second housing end 714. The piston 704 may include a first piston end 718 and a second piston end 720. The piston 704 may include a piston head 722 of larger outer diameter than the rest of the piston 704. The spring 706 may include a plurality of spring washers 726 as described above. The cap 708 may include a threaded section 724 configured for engaging a threaded section of the housing 702 at the first housing end 712. In the illustrated example, the cap's threaded section 724 is an outer section configured for mating with internal threads (not shown) of the housing bore 716. The housing 702 may also include a threaded section 725 (external threads in the present example) at the second housing end 714, which may be configured for engaging an external body (not shown) with which the fluid coupling device 700 is to interface.

The fluidic coupling device 700 may be assembled in the same or similar manner as the fluidic coupling device 200 described earlier in this disclosure and illustrated in FIGS. 2-6. In some embodiments, the fluidic coupling device 700 includes one or more pins 728, the housing 702 includes a like number of first pin passages 730, and the cap 708 includes one or more corresponding second pin passages (not shown). These components may cooperate to provide a locked position as described above. In some embodiments, the housing 702 includes one or more lateral apertures 732 as described above. In some embodiments, the housing 702 includes one or more gripping components 734 as described above.

Figure 9:
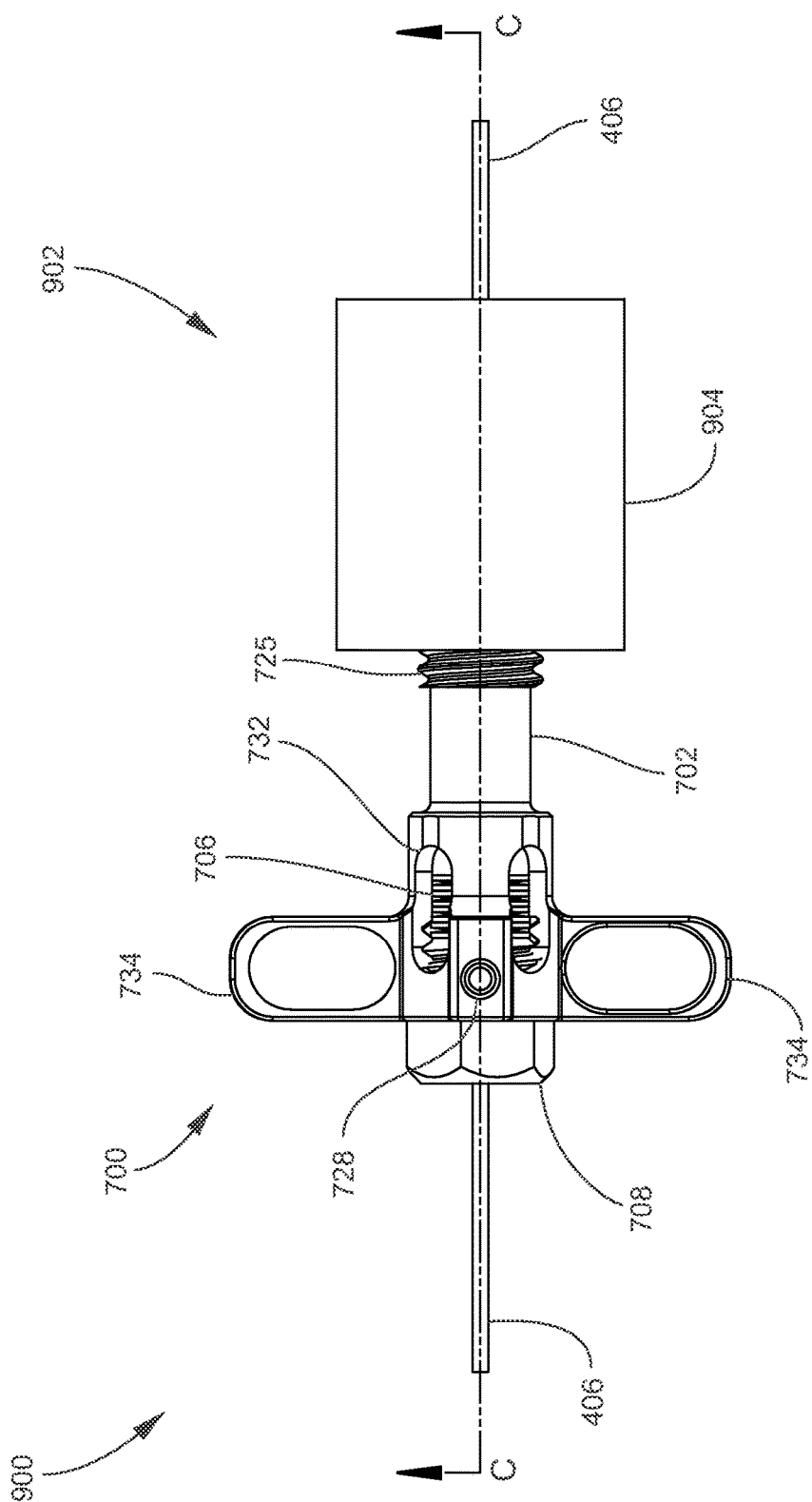
FIG. 9 is a side view of an example of a fluidic assembly formed by fluidly coupling the fluidic coupling device illustrated in FIGS. 7 and 8 to another component.

FIG. 9 is a side view of an example of a fluidic assembly 900 formed by fluidly coupling the fluidic coupling device 700 to another component 902. The component 902 is or includes a hollow body 904. A conduit 406 passes through the fluidic coupling device 700. The conduit 406 may pass through the body 904 as illustrated, or may instead extend through a portion of the body 904 in open communication with the body's interior. The body 904 may be associated with a chamber, analytical instrument, etc., as described above.

Figure 10:
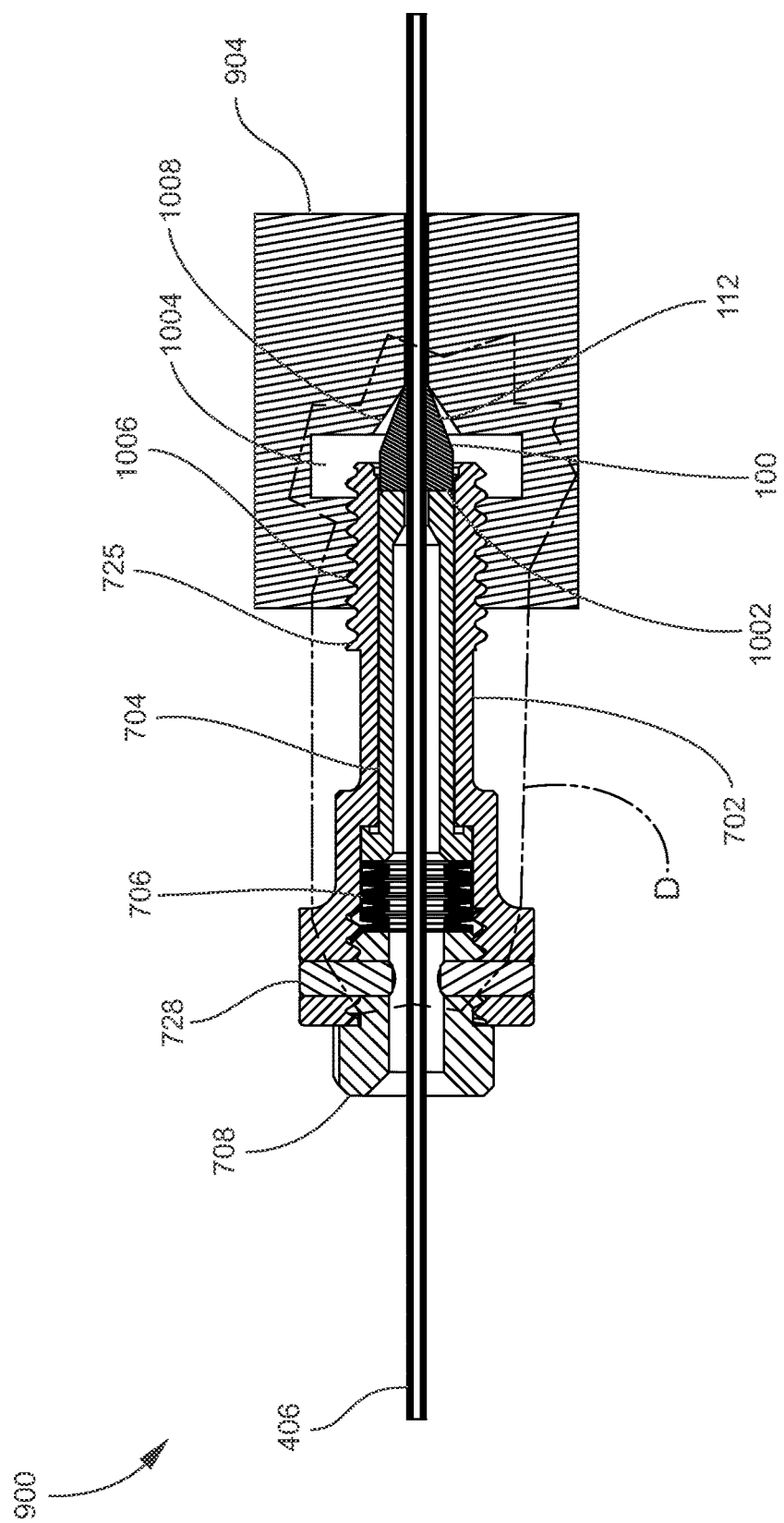
FIG. 10 is a cross-sectional view of the fluidic assembly taken along line C-C in FIG. 9.
Figure 11:
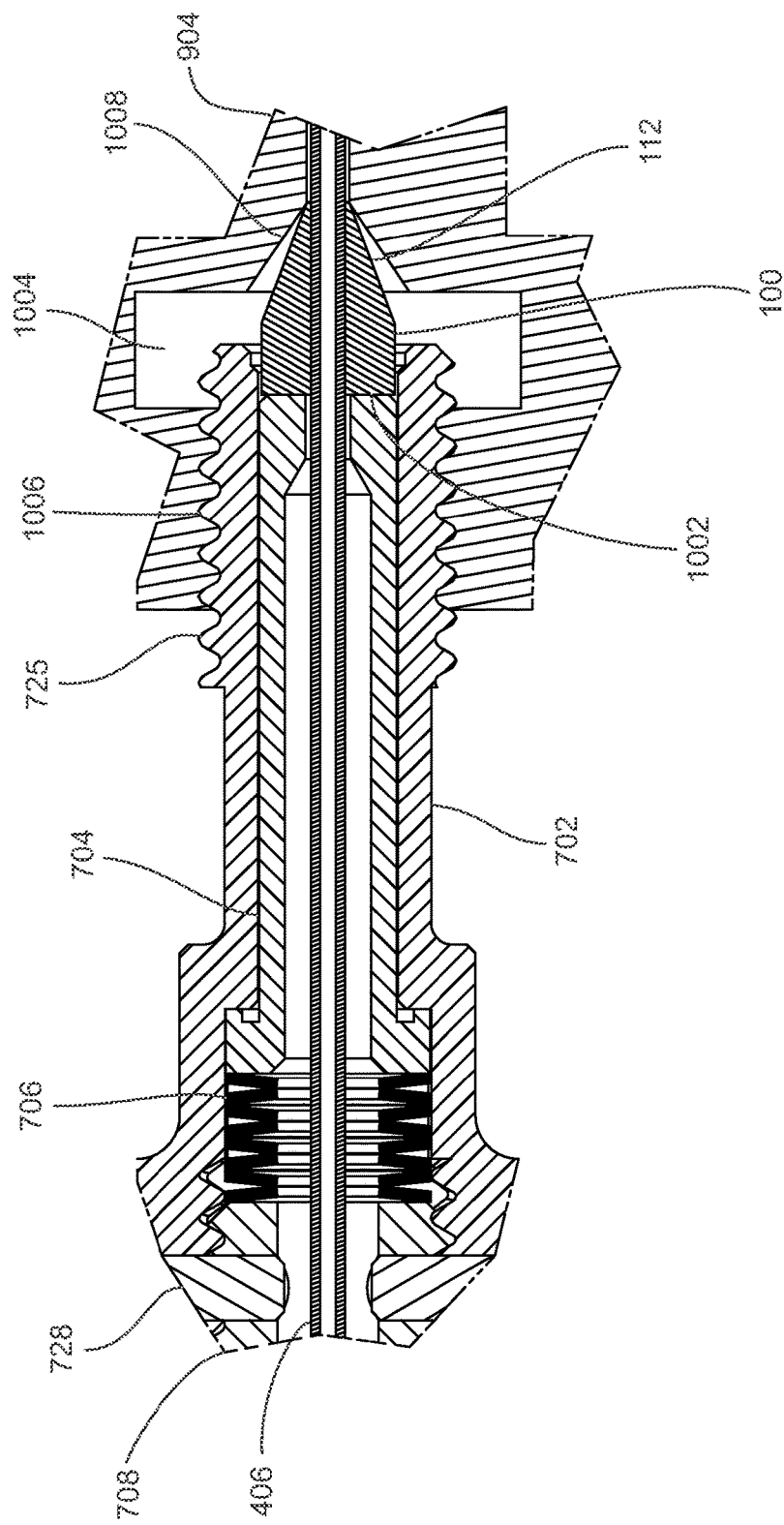
FIG. 11 is a detailed view of a region in FIG. 10 designated "D."

FIG. 10 is a cross-sectional view of the fluidic assembly 900 taken along line C-C in FIG. 9. FIG. 11 is a detailed view of a region in FIG. 10 designated "D." In this embodiment, the piston 704 includes a piston end surface 1002 at the second piston end, which is typically a flat surface. The body 904 has a body bore 1004 and a threaded section 1006. In the illustrated embodiment, the threaded section 1006 of the body 904 includes inner threads, and the outer threads of the threaded section 725 at the second housing end are configured to mate with the body's inner threads. Also in this embodiment, the body 904 includes a tapered inner surface 1008 that defines a portion of the body bore 1004. Thus, in this embodiment the orientation of the ferrule 100 is reversed as compared to the embodiment illustrated in FIGS. 2-6, with the tapered outer surface 112 facing the tapered inner surface 1008 of the body 904 and the opposing (typically flat) ferrule end surface facing the piston end surface 1002.

To make the fluidic coupling, the ferrule 100 is inserted into the housing bore from the second housing end in the orientation just noted. The coupling process may be implemented in the same or similar manner as that described above in conjunction with the embodiment of FIGS. 2-6. Rotation of the housing 702 compresses the spring 706. Rotation of the housing 702 also axially translates the piston 704 against the ferrule 100, which in turn translates the tapered outer surface 112 against the tapered inner surface 1008 of the body 904. Rotation of the housing 702 causes the tapered inner surface 1008 and the tapered outer surface 112 to be compressed together to form a fluidic seal therebetween, and the ferrule end surface and the piston end surface 1002 to be compressed together to form a fluidic seal therebetween. This compression in turn causes the ferrule 100 to bear down on the conduit 406. The cap 708 may also be rotated relative to the housing 702 to contribute to creation of the fluidic seals, as described above. The fluidic coupling device 700 is configured to provide a consistent, repeatable compressive load in a manner analogous to that described above in conjunction with FIGS. 2-6.

Figure 12:
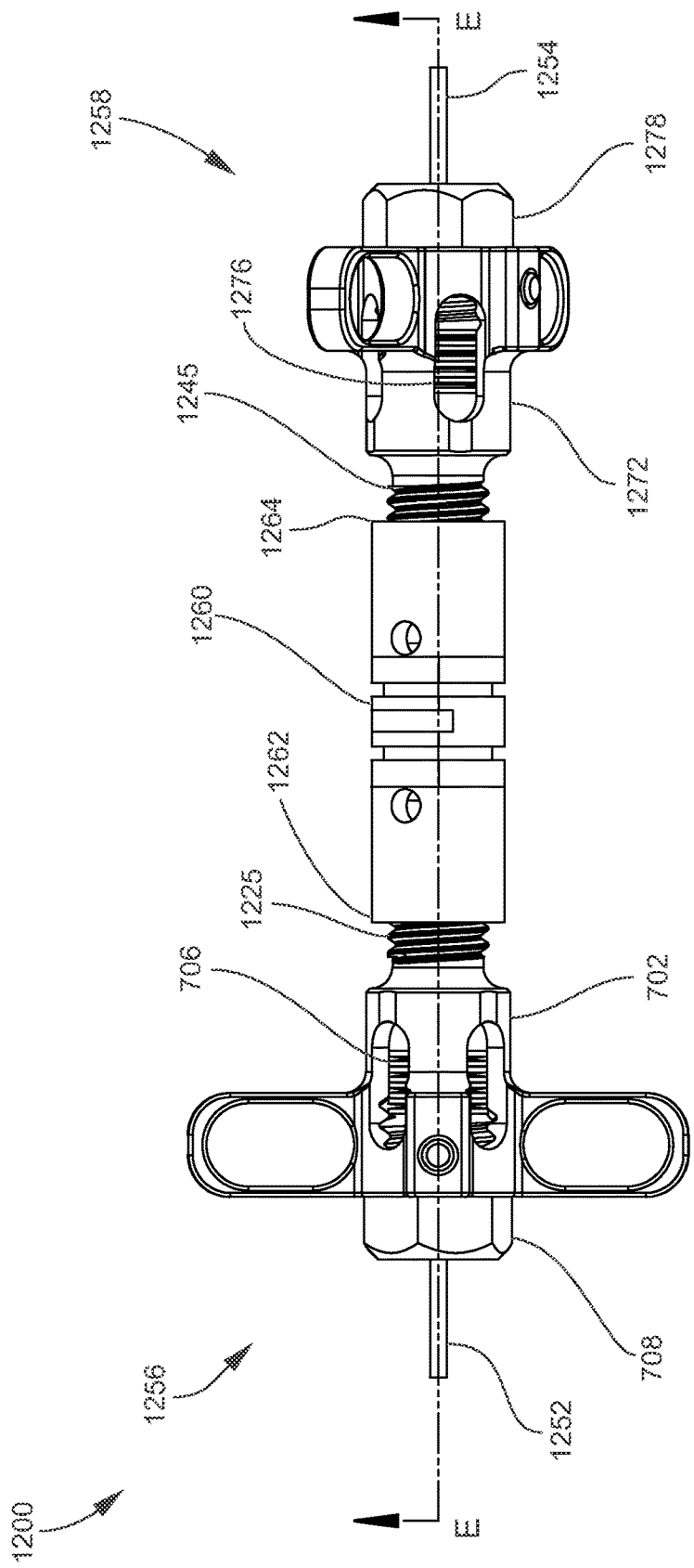
FIG. 12 is a side view of an example of a fluidic coupling device or assembly according to another embodiment.
Figure 13:
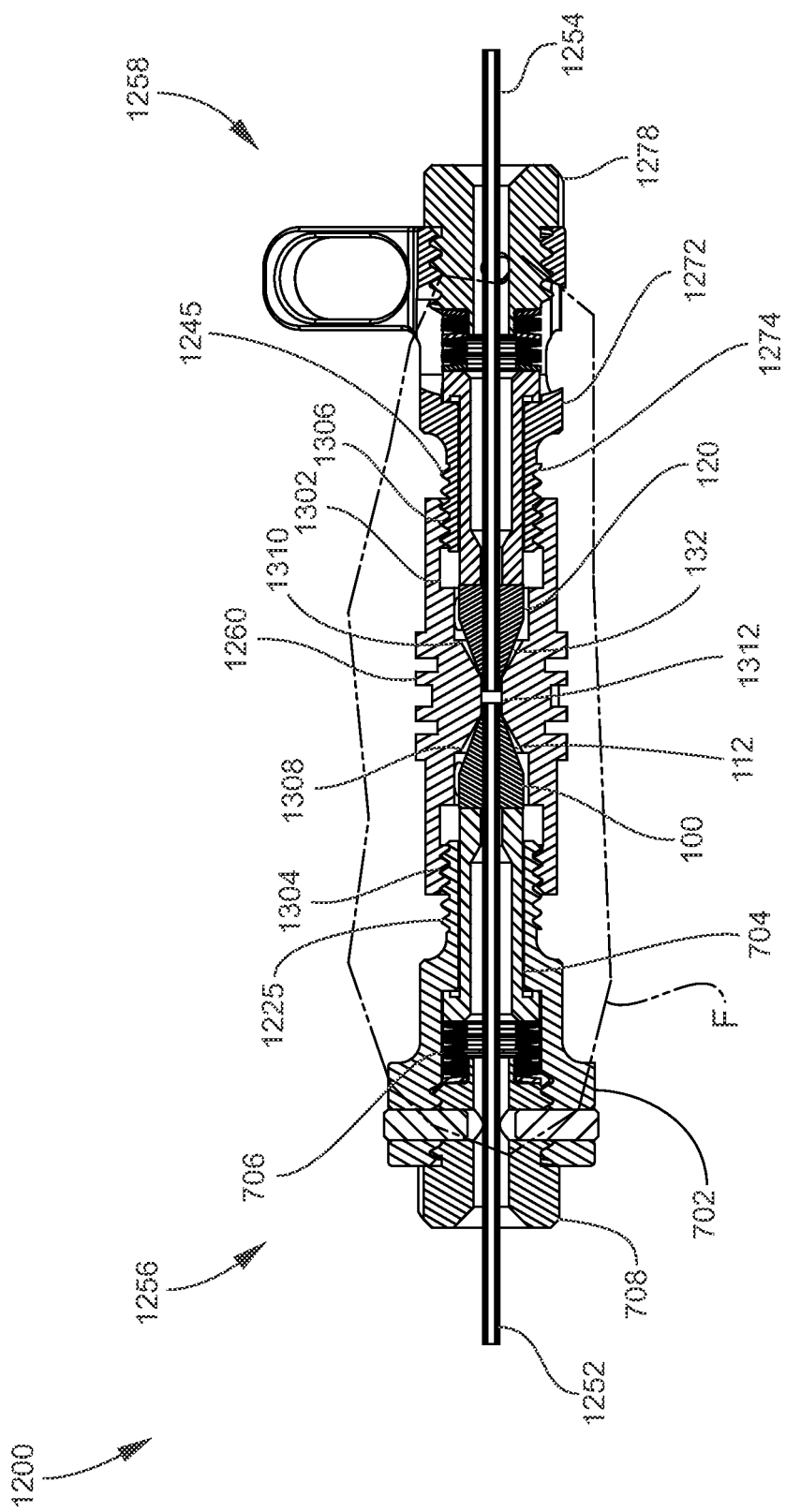
FIG. 13 is a cross-sectional view of the fluidic coupling assembly taken along line E-E in FIG. 12.
Figure 14:
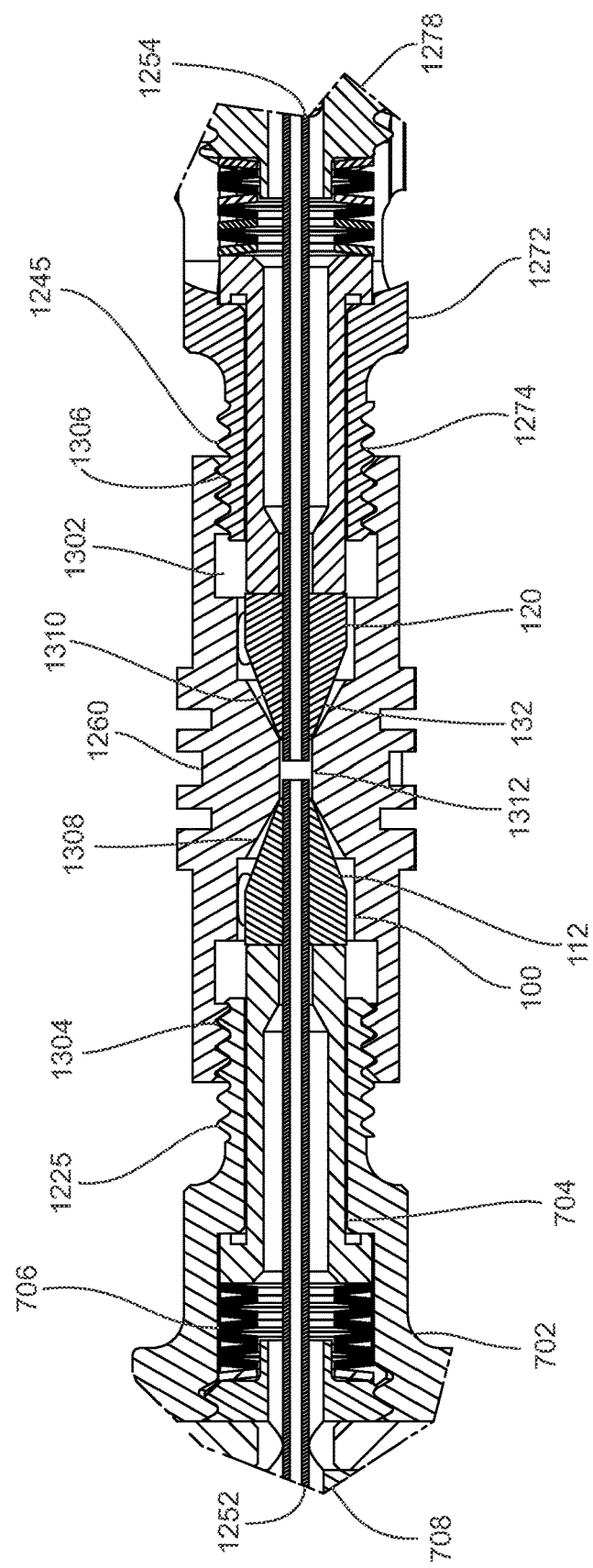
FIG. 14 is a detailed view of a region in FIG. 13 designated "F."

FIG. 12 is a side view of an example of a fluidic coupling device or assembly 1200 according to another embodiment. FIG. 13 is a cross-sectional view of the fluidic coupling assembly 1200 taken along line E-E in FIG. 12. FIG. 14 is a detailed view of a region in FIG. 13 designated "F." In this embodiment, the fluidic coupling assembly 1200 is configured for creating a fluid-tight joint between a first conduit 1252 and a second conduit 1254.

The fluidic coupling assembly 1200 includes a first fluidic coupling device 1256, a second fluidic coupling device 1258, and a body 1260. Each fluidic coupling device 1256 and 1258 may be configured and assembled in the same or similar manner as the fluidic coupling device 200 illustrated in FIGS. 2-6 or the fluidic coupling device 700 illustrated in FIGS. 7-11. By way of example, the fluidic coupling devices 1256 and 1258 illustrated in FIGS. 12-14 are configured similarly to the fluidic coupling device 700 illustrated in FIGS. 7-11.

Thus, in the illustrated embodiment the first fluidic coupling device 1256 may include a first housing 702, a first piston 704, a first spring 706, and a first cap 708. The first housing 702 may include a first housing end, a second housing end, and a first housing bore extending along a longitudinal axis of the fluidic coupling device 700 between the first housing end and the second housing end. The first piston 704 may include a first piston end and a second piston end. The first piston 704 may include a piston head of larger outer diameter than the rest of the first piston 704. The first spring 706 may include a plurality of spring washers as described above. The first cap 708 may include a threaded section configured for engaging a threaded section of the first housing 702 at the first housing end. Also in the illustrated embodiment, the second fluidic coupling device 1258 may include a second housing 1272, a second piston 1274, a second spring 1276, and a second cap 1278. The second housing 1272 may include a third housing end, a fourth housing end, and a second housing bore extending along the axis between the third housing end and the fourth housing end. The second piston 1274 may include a third piston end and a fourth piston end. The second piston 1274 may include a piston head of larger outer diameter than the rest of the second piston 1274. The second spring 1276 may include a plurality of spring washers as described above. The second cap 1278 may include a threaded section configured for engaging a threaded section of the second housing 1272 at the third housing end.

In this embodiment, the body 1260 serves as a union or joint. The body 1260 includes a first body end 1262, a second body end 1264, and a body bore 1302 extending along the axis of the fluid coupling assembly 1200. The body 1260 includes threaded sections 1304 and 1306 at the first body end 1262 and second body end 1264 configured for engaging threaded sections 1225 and 1245 of the first fluidic coupling device 1256 and second fluidic coupling device 1258, respectively. The body 1260 further includes a first tapered inner surface 1308 and a second tapered inner surface 1310 defining portions of the body bore 1302. The first tapered inner surface 1308 faces the first body end 1262, and the second tapered inner surface 1310 faces the second body end 1264. The body bore 1302 may include a central region 1312 of constant diameter between the first tapered inner surface 1308 and second tapered inner surface 1310.

To make the fluidic coupling, a first ferrule 100 is inserted into the body 1260 from the first body end 1262 such that the tapered outer surface 112 of the first ferrule 100 faces the first tapered inner surface 1308 of the body 1260. The first conduit 1252 is then inserted through the first fluidic coupling device 1256 and the first ferrule 100. The first conduit 1252 may be inserted far enough that it extends into the central region 1312 of the body bore 1302. The first fluidic coupling device 1256 is then threadedly engaged with the first body end 1262. The housing 702 of the first fluidic coupling device 1256 is then rotated to create fluid seals in the same or similar manner as that described above in conjunction with the embodiment of FIGS. 7-11. A second ferrule 120 is then inserted into the body 1260 from the second body end 1264 such that a tapered outer surface 132 of the second ferrule 120 faces the second tapered inner surface 1310 of the body 1260. The second conduit 1254 is then inserted through the second fluidic coupling device 1258 and the second ferrule 120. The second conduit 1254 may be inserted far enough that it extends into the central region 1312 of the body bore 1302. A gap in the central region 1312 between the first conduit 1252 and the second conduit 1254 may or may not remain after the coupling process is completed. The second fluidic coupling device 1258 is then threadedly engaged with the second body end 1264. The housing 1272 of the second fluidic coupling device 1258 is then rotated to create fluid seals in the same or similar manner as described above.

The order of one or more of the above-described steps may be varied. For example, both conduits 1252 and 1254 and ferrules 100 and 120 may be inserted into the body 1260 before operating either of the fluidic coupling devices 1256 and 1258 to apply compression.

In other embodiments, the fluidic coupling devices 1256 and 1258 illustrated in FIGS. 12-14 may be configured similarly to the fluidic coupling device 200 illustrated in FIGS. 2-6. In this case, the pistons 704 and 1274 may include the first and second tapered inner surfaces, respectively. The body 1260 may include (typically flat) end surfaces (in the place of the first and second tapered inner surfaces shown in FIGS. 13 and 14) respectively facing the ferrules' end surfaces that oppose the ferrules' tapered outer surfaces 112 and 132. The two ferrules 100 and 120 would thus be oriented in a reverse manner as compared to that shown in FIGS. 13 and 14.

According to other embodiments, a fluidic coupling kit may be provided. In some embodiments, the fluidic coupling kit may include the fluidic coupling device 200. In one embodiment, the fluidic coupling device 200 may be disassembled such as shown in FIG. 2. In another embodiment, the fluidic coupling device 200 may be assembled such as shown in FIG. 3. In the assembled fluidic coupling device 200, the spring 206 may or may not be pre-compressed, and the cap 208 may or may not be in a locked position. In other embodiments, one or more ferrules 100 and/or conduits 406 suitable for use with the fluidic coupling device 200 may additionally be included in the fluidic coupling kit. In various embodiments, the fluidic coupling kit may include a container in which the components are disposed. The container may be utilized for shipping the fluidic coupling kit to a user or storage of the fluidic coupling kit by the user. In various embodiments, the fluidic coupling kit may include instructions for use of the fluidic coupling device 200.

In other embodiments, the fluidic coupling kit may include the fluidic coupling device 700. The fluidic coupling device 700 may be disassembled such as shown in FIG. 7 or assembled such as shown in FIG. 8. In other embodiments, one or more ferrules 100 and/or conduits 406 may additionally be included. In various embodiments, the fluidic coupling kit may include a container, and may further include instructions for use.

In other embodiments, the fluidic coupling kit may include the fluidic coupling assembly 1200, with one or more fluidic coupling devices 1256 and 1258 and bodies 1260. The fluidic coupling devices 1256 and 1258 may initially be provided in assembled or disassembled form. The fluidic coupling devices 1256 and 1258 may initially be threadedly engaged with the body 1260. In use, the user may disengage the fluidic coupling devices 1256 and 1258 from the body 1260, insert ferrules, and then reattach the fluidic coupling devices 1256 and 1258. In other embodiments, one or more ferrules 100 and 120 and/or conduits 1252 and 1254 may additionally be included. In various embodiments, the fluidic coupling kit may include a container, and may further include instructions for use.

In other embodiments, the fluidic coupling kit may include a combination of one or more of the fluidic coupling devices, bodies, ferrules, conduits, etc. described above.

EXAMPLE

An example of a fluidic coupling device as presently disclosed herein (presently disclosed device) was tested and compared to an existing fluidic coupling device of a known configuration (known device). The presently disclosed device had a configuration consistent with that described above and illustrated in FIGS. 2-6, with the floating piston and spring system, and the ability to form fluidic connections by finger-tightening. The known device had a configuration that did not include a spring-loaded piston and requires wrench-tightening to form fluidic connections. Both the presently disclosed device and the known device utilized the same model of graphite/Vespel® polymer ferrules of known design commercially available from Agilent Technologies Inc., Santa Clara, Calif., USA. In both cases, the ferrules utilized were fresh, i.e., had not been previously used to form fluidic connections. The presently disclosed device was utilized to form new fluidic connections at the transfer line and GC inlet of a 5975C GC/MSD system commercially available from Agilent Technologies, Inc., Santa Clara, Calif., USA. Several experimental runs were performed on a specific sample material and chromatographic data was acquired. For comparison, the known device was utilized to form new fluidic connections at the transfer line and GC inlet of the same 5975C GC/MSD system, and several experimental runs were performed on the same sample material and chromatographic data was acquired.

FIGS. 15 and 16 provide examples of the chromatographic data (signal intensity over time) acquired during testing. Specifically, FIG. 15A is a chromatogram acquired from the first run utilizing the known device and known ferrule. By comparison, FIG. 15B is a chromatogram acquired after 25 sample injections that incorporated an equal number of thermal cycles with no changes to the chromatographic system. As clearly shown by arrows, a significant background contribution to the signal was detected, and was the result of air leaking from the fluidic connections formed from the known device and ferrule.

Figure 16A:
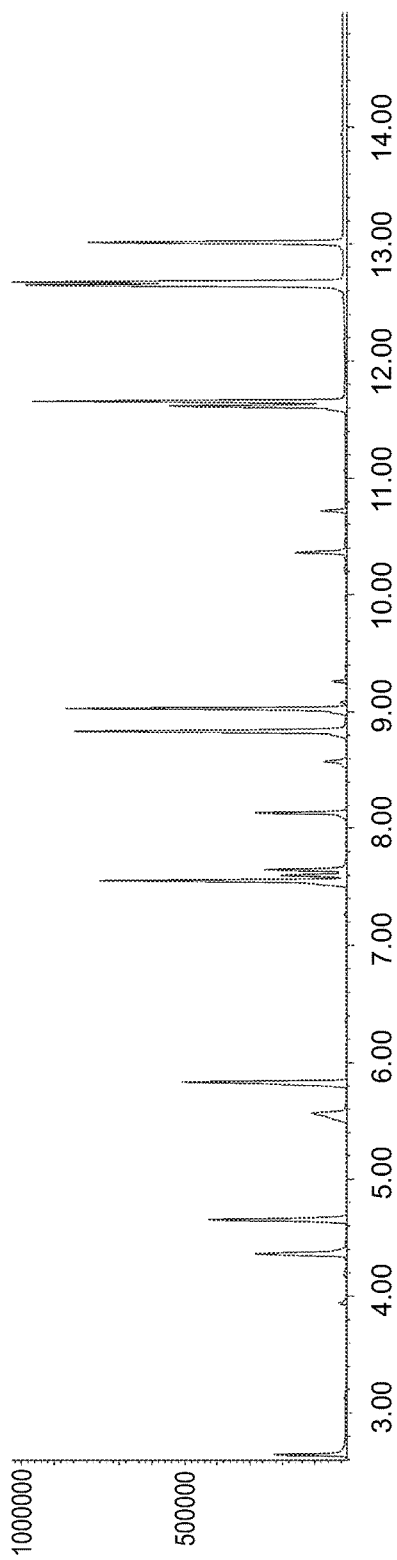
FIG. 16A is a chromatogram acquired from of a fluidic coupling device having a configuration as presently disclosed herein.
Figure 16B:
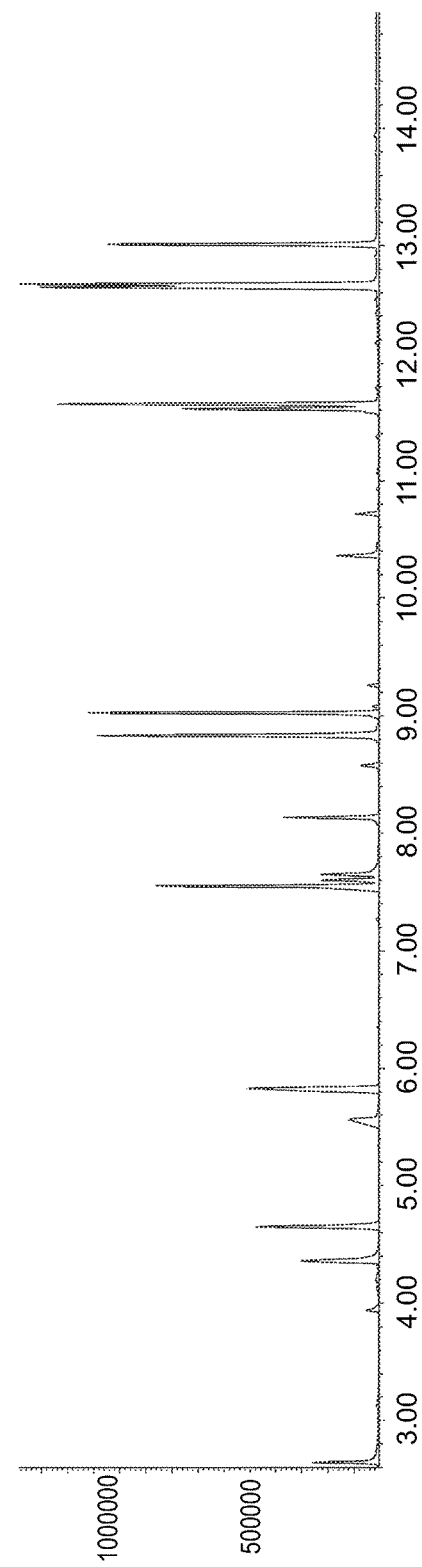
FIG. 16B is a chromatogram acquired during the same testing referred to above in conjunction with FIG. 16A, after over 300 sample injections.

FIG. 16A is a chromatogram acquired from the first run utilizing the presently disclosed device and known ferrule. By comparison, FIG. 16B is a chromatogram acquired after over 300 sample injections that incorporated an equal number of thermal cycles. No change in the background signal is observed. No re-tightening of the device was done between these runs. The data demonstrates that the presently disclosed device maintains reliable sealing performance over many cycles of use, without requiring the use of a tool to form the fitting and without requiring re-tightening between operations.

It will be understood that terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A fluidic coupling device, comprising:
    a housing comprising a first housing end, a second housing end, and a housing bore extending along an axis from the first housing end to the second housing end;
    a ferrule comprising a tapered outer surface and insertable into the housing bore;
    a piston insertable into the housing bore such that the piston contacts the ferrule;
    a spring comprising an axial series of spring washers and insertable into the housing bore such that the piston is between the spring and the ferrule; and
    a cap insertable into the housing bore and into contact with the spring, the cap being threadedly engageable with the first housing end, wherein rotation of the cap compresses the spring and translates the piston against the ferrule such that the tapered outer surface and a tapered inner surface are compressed together, and wherein the tapered inner surface is selected from the group consisting of: a tapered inner surface of the piston; and a tapered inner surface of a body attachable to the second housing end.

2. The fluidic coupling device of claim 1, comprising a conduit extending through respective bores of the cap, the spring, the piston and the ferrule, wherein compression of the tapered outer surface and the tapered inner surface together compresses the ferrule against the conduit.

3. The fluidic coupling device of claim 1, comprising the body, wherein:
the body comprises a first body end, a second body end, a body bore extending along the axis from the first body end to the second body end, a first tapered inner surface facing the first body end, and a second tapered inner surface facing the second body end, and wherein:
the housing is a first housing and the housing bore is a first housing bore, wherein the second housing end is threadedly engageable with the first body end;
the ferrule is a first ferrule and the tapered outer surface is a first tapered outer surface, wherein the first ferrule is insertable into the body bore such that the first tapered outer surface faces the first tapered inner surface;
the piston is a first piston;
the spring is a first spring comprising an axial series of first spring washers; and
the cap is a first cap,
wherein the fluidic coupling assembly further comprises:
a second housing comprising a third housing end, a fourth housing end, and a second housing bore extending along the axis from the third housing end to the fourth housing end, wherein the fourth housing end is threadedly engageable with the second body end;
a second ferrule comprising a second tapered outer surface, wherein the second ferrule is insertable into the body bore such that the second tapered outer surface faces the second tapered inner surface;
a second piston insertable into the second housing bore such that the second piston contacts the second ferrule;
a second spring comprising an axial series of second spring washers and insertable into the second housing bore such that the second piston is between the second spring and the second ferrule; and
a second cap insertable into the housing bore and into contact with the second spring, the second cap being threadedly engageable with the third housing end, wherein rotation of the second cap compresses the second spring and translates the second piston against the second ferrule such that the second tapered outer surface and the second tapered inner surface are compressed together.

4. A fluidic assembly, comprising:
the fluidic coupling device of claim 1;
a body comprising a body bore and threadedly engageable with the second housing end; and
a conduit extending through respective bores of the cap, the spring, the piston, and the ferrule such that the conduit communicates with or extends into the body bore,
wherein rotation of the housing relative to the body compresses the tapered outer surface and the tapered inner surface together to form a fluidic seal therebetween, and compresses the ferrule against the conduit.

5. The fluidic assembly of claim 4, wherein the piston comprises the tapered inner surface, the ferrule comprises an end surface opposite to the tapered outer surface, the body comprises a body surface, and rotation of the housing translates the end surface into contact with the body surface.

6. The fluidic assembly of claim 4, wherein the body comprises the tapered inner surface, the ferrule comprises a ferrule end surface opposite to the tapered outer surface, the piston comprises a piston end surface, and rotation of the housing translates the piston end surface into contact with the ferrule end surface.

7. A fluidic coupling device, comprising:
a housing comprising a first housing end, a second housing end, and a housing bore extending along an axis from the first housing end to the second housing end;
a piston disposed in the housing bore;
a spring comprising an axial series of spring washers disposed in the housing bore; and
a cap disposed in the housing bore wherein the spring is between the cap and the piston, the cap threadedly engaged with the first housing end.

8. The fluidic coupling device of claim 7, wherein the housing comprises a first passage oriented at an angle to the axis, the cap comprises a second passage and is threadedly engaged with the first housing end to a locked position at which the first passage is aligned with the second passage, and further comprising a pin extending through the first passage and the second passage, wherein the pin retains the cap in the locked position.

9. The fluidic coupling device of claim 7, wherein the housing comprises a protrusion in the housing bore, and at a locked position the piston contacts the protrusion and the spring is compressed between the cap and the piston.

10. The fluidic coupling device of claim 7, wherein the piston comprises a tapered inner surface at an end of the piston opposite to the spring.

11. A fluidic coupling kit, comprising:
one or more fluidic coupling devices according to claim 7; and
a body comprising a first body end, a second body end, and a body bore extending along the axis from the first body end to the second body end,
wherein the second housing end of each fluidic coupling device is threadedly engageable with a selected one of the first body end and the second body end.

12. The fluidic coupling kit of claim 11, wherein the body comprises a first tapered inner surface facing the first body end and a second tapered inner surface facing the second body end.

13. The fluidic coupling kit of claim 12, comprising one or more ferrules, each ferrule comprising a tapered outer surface and insertable into the body bore such that the tapered outer surface faces a selected one of the first tapered inner surface and the second tapered inner surface, wherein rotation of the housing at the selected first body end or second body end compresses the ferrule against the selected first tapered inner surface or second tapered inner surface.

14. A method for making a fluidic coupling, the method comprising:
inserting a ferrule into a fluidic coupling device, the fluidic coupling device comprising:
a housing comprising a first housing end, a second housing end, and a housing bore extending along an axis from the first housing end to the second housing end, wherein inserting the ferrule inserts the ferrule into the housing bore,
a piston insertable into the housing bore such that the piston contacts the ferrule,
a spring comprising an axial series of spring washers and insertable into the housing bore, and a cap insertable into the housing bore and into contact with the spring,
wherein the piston is disposed in the housing between the spring and the ferrule, and the cap is threadedly engaged with the first housing end;
inserting a conduit through respective bores of the cap, the spring, the piston and the ferrule;
threadedly engaging the second housing end with a body such that the conduit extends into an interior of the body; and
forming a fluidic seal between the ferrule and the piston and between the ferrule and the body by rotating the housing relative to the body,
wherein rotating the housing compresses the spring between the cap and the piston, compresses the ferrule against the conduit, and compresses a tapered outer surface of the ferrule against a tapered inner surface, and wherein the tapered inner surface is selected from the group consisting of: a tapered inner surface of the piston; and a tapered inner surface of the body.

15. The method of claim 14, wherein rotating comprises manipulating a gripping component of the housing.

16. The method of claim 14, comprising rotating the cap relative to the housing to compress the spring.

17. The method of claim 16, comprising rotating the cap to an extent that compresses the tapered outer surface against the tapered inner surface.

18. The method of claim 14, wherein the piston comprises the tapered inner surface, and rotation of the housing translates the tapered inner surface into contact with the tapered outer surface.

19. The method of claim 14, wherein the body comprises the tapered inner surface, and rotation of the housing translates the tapered outer surface into contact with the tapered inner surface.

20. The method of claim 14, wherein:
the ferrule is a first ferrule, the fluidic coupling device is a first fluidic coupling device, the housing is a first housing, the piston is a first piston, the cap is a first cap comprising an axial series of spring washers, and the conduit is a first conduit;
the body comprises a first body end, a second body end, a first tapered inner surface in the interior and facing the first body end, and a second first tapered inner surface in the interior and facing the second body end;
threadedly engaging the second housing end with the body comprises threadedly engaging the second housing end with the first body end; and
rotating the first housing compresses the tapered outer surface of the first ferrule against the first tapered inner surface,
wherein the method further comprises:
inserting a second ferrule into a second fluidic coupling device, the second fluidic coupling device comprising a second housing, a second piston, a second spring, and a second cap, wherein the second piston is disposed in the second housing between the second spring and the second ferrule, and the second cap is threadedly engaged with a third housing end of the second housing;
inserting a second conduit through respective bores of the second cap, the second spring, the second piston and the second ferrule;
threadedly engaging a fourth housing end of the second housing with the second body end such that the conduit extends into an interior of the second body; and
forming a fluidic seal between the second ferrule and the second piston and between the second ferrule and the body by rotating the second housing relative to the body,
wherein rotating the second housing compresses the second spring between the second cap and the second piston, compresses the second ferrule against the second conduit, and compresses a tapered outer surface of the second ferrule against the second tapered inner surface, and wherein the first conduit fluidly communicates with the second conduit in the body.

* * * * *